United States Patent
Eastman et al.

(10) Patent No.: US 9,316,554 B1
(45) Date of Patent: Apr. 19, 2016

(54) FIBER OPTIC ANALYTE SENSOR WITH INTEGRATED IN SITU TOTAL PRESSURE CORRECTION

(71) Applicant: MOCON, INC, Minneapolis, MN (US)

(72) Inventors: John Eastman, Rogers, MN (US); Daniel W. Mayer, Wyoming, MN (US)

(73) Assignee: MOCON, INC., Minneapolis, MN (US)

(*) Notice: Subject to any disclaimer, the term of this patent is extended or adjusted under 35 U.S.C. 154(b) by 0 days.

(21) Appl. No.: 14/580,873

(22) Filed: Dec. 23, 2014

(51) Int. Cl.

| | |
|---|---|
| *G01N 21/64* | (2006.01) |
| *G01N 1/22* | (2006.01) |
| *G01L 19/00* | (2006.01) |
| *G01N 33/15* | (2006.01) |
| *G01N 33/02* | (2006.01) |
| *G01N 33/00* | (2006.01) |
| *G01N 21/77* | (2006.01) |
| *G01N 21/76* | (2006.01) |

(52) U.S. Cl.
CPC ............ *G01L 19/0092* (2013.01); *G01N 21/64* (2013.01); *G01N 33/02* (2013.01); *G01N 33/15* (2013.01); *G01N 1/2226* (2013.01); *G01N 21/766* (2013.01); *G01N 21/7703* (2013.01); *G01N 33/004* (2013.01); *G01N 2201/061* (2013.01); *G01N 2201/08* (2013.01); *Y10T 436/207497* (2015.01)

(58) Field of Classification Search
CPC ....... G01N 1/22; G01N 1/2226; G01N 21/62; G01N 21/64; G01N 21/6428; G01N 21/76; G01N 21/766; G01N 21/7703; G01N 33/004; Y10T 436/20; Y10T 436/204998; Y10T 436/207497; Y10T 436/25875

USPC ........... 436/68, 127, 133, 136, 148, 164, 165, 436/167, 169, 172, 181; 422/416, 417, 420, 422/68.1, 82.05, 82.08, 82.13, 83, 88, 91
See application file for complete search history.

(56) References Cited

U.S. PATENT DOCUMENTS

| | | | |
|---|---|---|---|
| 3,138,937 | A | 6/1964 | Parkinson et al. |
| 4,622,974 | A | 11/1986 | Coleman et al. |

(Continued)

FOREIGN PATENT DOCUMENTS

| | | |
|---|---|---|
| CA | 2600563 A1 | 9/2006 |
| EP | 1887344 A1 | 2/2008 |

(Continued)

OTHER PUBLICATIONS

Multisorb Technologies, FRESHPAX, Oxygen Absorbing Packets and Strips, 2009.

(Continued)

*Primary Examiner* — Maureen Wallenhorst
(74) *Attorney, Agent, or Firm* — Sherrill Law Offices, PLLC (57) ABSTRACT

A fiber optic analyte sensing needle employing an analyte-partial-pressure-sensitive photoluminescent probe, characterized by (i) a void volume channel extending axially along the length of the lumen between the inner surface of the tube and the outer surface of the fiber optic filament, and (ii) a total pressure sensor in pressure communication with the distal tip of the needle via the void volume channel, whereby total pressure of a volume sampled by the sensing needle can be routinely measured and used in pressure compensation of analyte-concentration values calculated from the analyte-partial-pressure readings taken from the analyte-partial-pressure-sensitive photoluminescent probe.

19 Claims, 4 Drawing Sheets

(56) References Cited

U.S. PATENT DOCUMENTS

| | | | |
|---|---|---|---|
| 4,784,811 A | 11/1988 | Hirschfeld | |
| 5,173,432 A * | 12/1992 | Lefkowitz | G01N 21/6428 |
| | | | 250/458.1 |
| 5,230,427 A | 7/1993 | Betts et al. | |
| 5,328,823 A | 7/1994 | Spencer et al. | |
| 5,333,609 A | 8/1994 | Bedingham et al. | |
| 5,885,843 A | 3/1999 | Ayers et al. | |
| 6,328,932 B1 | 12/2001 | Carter et al. | |
| 8,173,438 B1 | 5/2012 | Putman et al. | |
| 2003/0221477 A1 | 12/2003 | Pierskalla et al. | |
| 2003/0235513 A1 | 12/2003 | Asai et al. | |
| 2005/0113658 A1* | 5/2005 | Jacobson | A61B 5/14532 |
| | | | 600/342 |
| 2006/0144811 A1 | 7/2006 | Cheng | |
| 2008/0072992 A1 | 3/2008 | Baleriaux et al. | |
| 2008/0146902 A1 | 6/2008 | Hacker et al. | |
| 2008/0199360 A1 | 8/2008 | Shahriari | |
| 2009/0075321 A1 | 3/2009 | Obeid et al. | |
| 2009/0084156 A1 | 4/2009 | Matsuda et al. | |
| 2009/0326344 A1 | 12/2009 | Meyer | |
| 2010/0116017 A1 | 5/2010 | Mayer et al. | |
| 2011/0223678 A1 | 9/2011 | Ascheman et al. | |
| 2012/0129268 A1 | 5/2012 | Mayer | |
| 2012/0295364 A1 | 11/2012 | Papkovsky et al. | |
| 2013/0177480 A1 | 7/2013 | Fernandes et al. | |
| 2013/0251593 A1 | 9/2013 | Eastman | |

FOREIGN PATENT DOCUMENTS

| | | |
|---|---|---|
| EP | 2336753 A2 | 6/2011 |
| EP | 1864118 B1 | 6/2012 |
| WO | 92/19150 | 11/1992 |
| WO | 2005/045385 A2 | 5/2005 |
| WO | 2006/095191 A1 | 9/2006 |

OTHER PUBLICATIONS

Papkovsky, Dmitri et al., "Biosensors on the basis of luminescent oxygen sensor: the use of microporous light-scattering support materials", Biochemestry Department, National University of Ireland, Cork, Elsevier, 1998. pp. 137-145.

* cited by examiner

FIBER OPTIC ANALYTE SENSOR WITH INTEGRATED IN SITU TOTAL PRESSURE CORRECTION

BACKGROUND

Photoluminescent sensors or probes are a widely employed method of measuring analyte concentration, typically oxygen, within a defined space, typically an enclosed space such as the headspace of a package or container. See, for example United States Published Patent Applications 2009/0029402, 2008/8242870, 2008/215254, 2008/199360, 2008/190172, 2008/148817, 2008/146460, 2008/117418, 2008/0051646, and 2006/0002822, and U.S. Pat. Nos. 7,569,395, 7,534,615, 7,368,153, 7,138,270, 6,689,438, 5,718,842, 4,810,655, and 4,476,870.

Briefly, analyte concentration within a package or container can be measured by placing an analyte-sensitive photoluminescent probe within the package or container, allowing the probe to equilibrate within the package or container, exciting the probe with radiant energy, and measuring the extent to which radiant energy emitted by the excited probe is quenched by the presence of the target analyte. Such optical sensors are available from a number of suppliers, including PreSens Precision Sensing, GmbH of Regensburg, Germany, Oxysense of Dallas, Tex., United States, and Mocon, Inc. of Minneapolis, Minn., United States.

In order to permit impromptu testing of a defined space, the photoluminescent probe can be provided as a coating on the distal tip of a fiber optic filament which is threaded into the lumen of a needle and protectively retained in a fixed position within the lumen by a target analyte permeable encapsulant. One example of such a fiber optic sensing needle for use in measuring the concentration of oxygen within living tissue is described in United States Patent Application Publication US 2009/0075321, the entire disclosure of which is hereby incorporated by reference.

While fiber optic sensing needles, such as that described in US 2009/0075321, are effective for impromptu measurement of analyte concentration within a defined space, they can result in inaccurate measurements when the total pressure within the defined space is significantly different than the environment surrounding the defined spaced as the fiber optic sensing needles measure analyte partial pressure—not concentration of analyte, from which a concentration of analyte is then calculated using the general equation $\text{ANALYTE \%} = P_{ANALYTE}/P_{TOTAL}$. Hence, lack of an accurate assumption as to the total pressure $P_{TOTAL}$ of the defined space can result in an inaccurately calculated analyte concentration.

Hence, a need exists for a fast response fiber optic sensing needle that can quickly and easily measure both analyte partial pressure $P_{ANALYTE}$ and total pressure $P_{TOTAL}$ in a defined space and thereby consistently provide a pressure correct measurement of analyte concentration ($\text{ANALYTE \%}$).

SUMMARY OF THE INVENTION

The invention is a fiber optic analyte-sensing instrument, method of measuring analyte concentration within an enclosed space using the fiber optic analyte-sensing instrument, and method for monitoring changes in analyte concentration within an enclosed space using the fiber optic analyte-sensing instrument.

A first embodiment of the instrument is an in situ analyte-sensing fiber optic instrument that includes (i) a tube defining a lumen, (ii) an analyte-partial-pressure-sensitive photoluminescent probe located proximate a distal end of the lumen and in fluid communication with a volume external to the distal end of the tube, and (iii) at least one fiber optic filament extending axially along the length of the lumen and in optical communication with the analyte-partial-pressure-sensitive photoluminescent probe. The instrument is characterized by (A) a void volume channel extending axially along the length of the lumen between the inner surface of the tube and the outer surface of the at least one fiber optic filament, and (B) a pressure sensor in pressure communication with the fluid communicating with the analyte-partial-pressure-sensitive photoluminescent probe via the void volume channel in the lumen of the tube. The pressure sensor permits pressure compensation of analyte-concentration values calculated from analyte-partial-pressure readings taken from the analyte-partial-pressure-sensitive photoluminescent probe.

The first embodiment of the instrument preferably has a pressure sensor that generates a $P_{TOTAL}$ electronic signal representative of the total-pressure of a fluid in fluid communication with the probe, and further includes (1) a detector in optical communication with the analyte-partial-pressure-sensitive photoluminescent probe via the at least one fiber optic filament for receiving radiant energy emitted by the probe and generating a $P_{ANALYTE}$ electrical signal representative of the analyte-partial-pressure of a fluid in fluid communication with the probe, and (2) a microprocessor in electrical communication with the pressure sensor and the detector for receiving temporally paired $P_{TOTAL}$ and $P_{ANALYTE}$ electrical signals respectively, and calculating an analyte concentration from the temporally paired electrical signals based upon the algorithm $\text{ANALYTE \%} = P_{ANALYTE}/P_{TOTAL}$, and (3) an electronic display in electrical communication with the microprocessor for displaying calculated analyte concentration values.

A second embodiment of the instrument is a handheld instrument for impromptu in situ concomitant sensing of analyte partial pressure, preferably oxygen partial pressure, and total pressure of a hermetically sealed volume that includes an integrated combination (i) a hollow shank having a proximal and distal ends with a lumen in fluid communication with a volume external to the distal end, (ii) an oxygen-partial-pressure-sensitive photoluminescent probe within the lumen proximate the distal end of the shank and in fluid communication with a volume external to the distal end of the shank, (iii) an electronics package proximate the proximal end of the shank that includes ($\alpha$) a source of excitation radiant energy, ($\beta$) a photoluminescence detector, and ($\gamma$) a pressure sensor, and (iv) at least one fiber optic filament extending axially along the length of the lumen operable for ($\alpha$) transmitting excitation radiant energy from the source of excitation radiant energy to the oxygen-partial-pressure-sensitive photoluminescent probe, and ($\beta$) transmitting radiant energy emitted by the oxygen-partial-pressure-sensitive photoluminescent probe to the photoluminescence detector, and configured relative to the lumen to form a void volume channel extending axially along the length of the lumen between the inner surface of the shank and the outer surface of the at least one fiber optic filament, wherein the pressure sensor is in pressure communication with the fluid communicating with the analyte-partial-pressure-sensitive photoluminescent probe via the void volume channel in the lumen of the shank.

The second embodiment of the instrument preferably has an electronics package that includes a photoluminescence detector that generates a $P_{ANALYTE}$ electrical signal representative of the analyte-partial-pressure of a fluid in fluid communication with the probe, and a pressure sensor that generates a $P_{TOTAL}$ electronic signal representative of the total-pressure of a fluid in fluid communication with the probe. The electronics package preferably further includes (i) a microprocessor in electrical communication with the photoluminescence detector and the pressure sensor for receiving temporally paired $P_{ANALYTE}$ and $P_{TOTAL}$ electrical signals respectively, and calculating an analyte concentration from the temporally paired electrical signals based upon the algorithm ANALYTE $\% = P_{ANALYTE}/P_{TOTAL}$, and (ii) an electronic display in electrical communication with the microprocessor for displaying calculated analyte concentration values.

The method of measuring analyte concentration within a space enclosed by a structure includes the steps of: (1) obtaining an analyte-sensing fiber optic instrument according to the invention, (2) penetrating the structure with the tube of the instrument so as to place the distal end of the lumen into fluid communication with the space enclosed by the structure, whereby both the analyte-partial-pressure-sensitive photoluminescent probe and the pressure sensor on the instrument are placed into sensible communication with the enclosed space, (3) allowing the concentration of analyte in sensible communication with the photoluminescent probe to equilibrate with the analyte concentration within the enclosed space, (4) allowing the pressure in sensible communication with the pressure sensor to equilibrate with the pressure of the enclosed space, and (5) ascertaining an analyte concentration within the enclosed space by: (i) measuring the total pressure of the enclosed space with the equilibriated pressure sensor, (ii) exposing the equilibriated photoluminescent probe to excitation radiation, (iii) measuring radiation emitted by the excited photoluminescent probe, and (iv) converting the measured emission to an oxygen concentration based upon a known pressure compensated conversion algorithm that employs the value of the measured total pressure of the enclosed space.

The method for monitoring changes in analyte concentration within a space enclosed by a structure includes the steps of (1) obtaining an analyte-sensing fiber optic instrument according to the invention, (2) penetrating the structure with the hollow shank of the instrument so as to place the distal end of the lumen into fluid communication with the space enclosed by the structure, whereby both the analyte-partial-pressure-sensitive photoluminescent probe and the pressure sensor on the instrument are placed into sensible communication with the enclosed space, (3) allowing the concentration of analyte in sensible communication with the photoluminescent probe to equilibrate with the analyte concentration within the enclosed space, (4) allowing the pressure in sensible communication with the pressure sensor to equilibrate with the pressure of the enclosed space, (5) ascertaining an analyte concentration within the enclosed space over time by: ($\alpha$) coincidentally and repeatedly measuring the total pressure of the enclosed space with the equilibriated pressure sensor, and the partial pressure of analyte in the enclosed spaced with the equilibriated photoluminescent probe, ($\beta$) measuring passage of time during the repeated coincidental measurements, and ($\gamma$) converting at least some of the coincidental measurements to an analyte concentration based upon a known pressure compensated conversion algorithm that employs the value of the measured total pressure of the enclosed space, and (6) reporting at least one of ($\alpha$) at least two ascertained analyte concentrations and the time interval between those reported concentrations, and ($\beta$) a rate of change in analyte concentration within the enclosed space calculated from data obtained in step (5).

DETAILED DESCRIPTION OF A PREFERRED EMBODIMENT

Nomenclature

10 Fiber Optic Analyte-Sensing Instrument
10a Collared Needle Subassembly of Instrument
10b Optical Block Subassembly of Instrument
10c Handle Portion of Instrument
20 Tube or Hollow Shank (Collectively Needle)
$20_1$ Proximal End of Needle
$20_2$ Distal End of Needle
$20_3$ Inner Surface of Needle
28 Ports in Needle
29 Lumen of Needle
$29_1$ Proximal End of Lumen
$29_2$ Distal End of Lumen
30 Collar
40 Thread Fitting
41 Outer O-Ring
42 Inner O-Ring
50 Fiber Optic Filament
$50_1$ Proximal End of Fiber Optic Filament
$50_2$ Distal End of Fiber Optic Filament
$50_4$ Outer Surface of Fiber Optic Filament
60 Void Volume Channel Sealing O-Rings
68 Void Volume Channel
69 Branch Channel
70 Photoluminescent Analyte-Partial-Pressure-Sensitive Probe
80 Photoluminescence Detector
81 Source of Excitation Radiant Energy
90 Pressure Sensor
100 Microprocessor
110 Display
120 Activation Trigger
S Structure
V Volume Enclosed by Structure

DESCRIPTION

Construction

Figure 1:
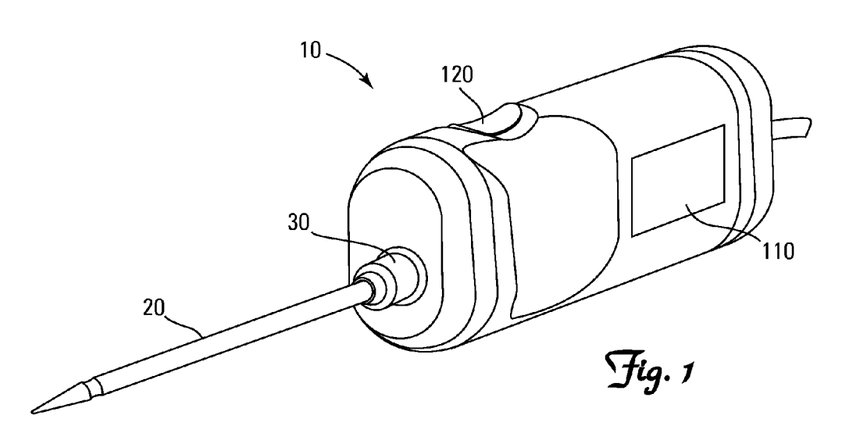
FIG. 1 is a perspective view of one embodiment of the invention.

Referring generally to FIG. 1, the invention is a fiber optic analyte-sensing instrument 10 employing a photoluminescent analyte-partial-pressure-sensitive probe 70 located proximate the distal end $20_2$ of a needle 20 having a lumen 29, and at least one fiber optic filament 50, preferably a single nonjacketed fiber, that extends axially along the length of the lumen 29. The instrument 10 is characterized by a void volume channel 68 that extends along the length of the lumen 29 between the inner surface $20_3$ of the needle 20 and the outer surface $50_4$ of the at least one fiber optic filament 50, and a pressure sensor 90 in pressure communication with the same fluid communicating with the photoluminescent analyte-partial-pressure-sensitive probe 70 via the void volume channel 68. The pressure sensor 90 permits pressure compensation of analyte-concentration values calculated from analyte-partial-pressure readings taken from the photoluminescent analyte-partial-pressure-sensitive probe 70.

The instrument 10 is capable of measuring a variety of analytes including oxygen ($O_2$) and carbon dioxide ($CO_2$), with oxygen of most widespread interest.

Figure 2:
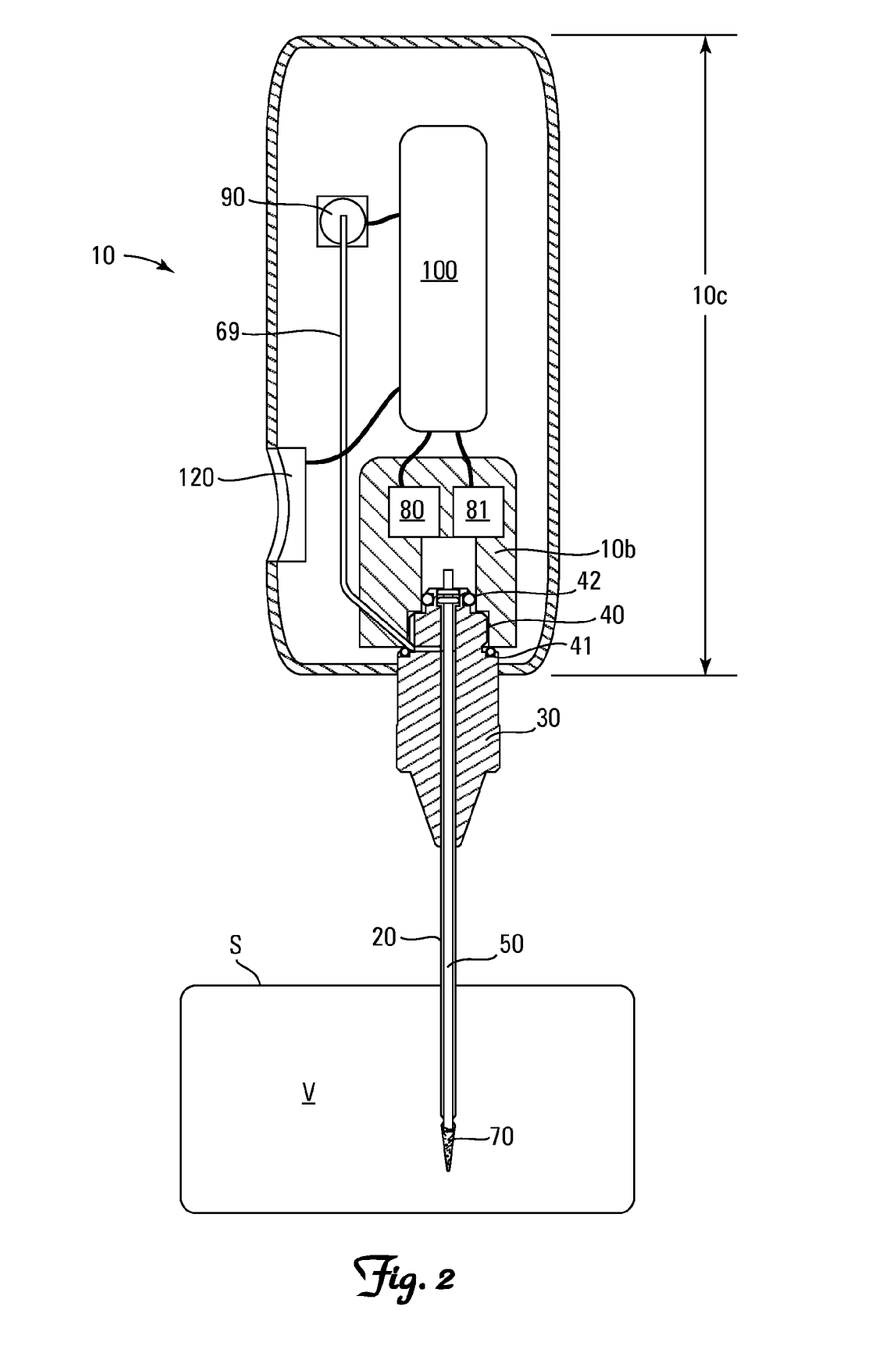
FIG. 2 is a cross-sectional side view of the invention depicted in FIG. 1 penetrating a structure with schematic depiction of the electronic components of the instrument.
Figure 3:
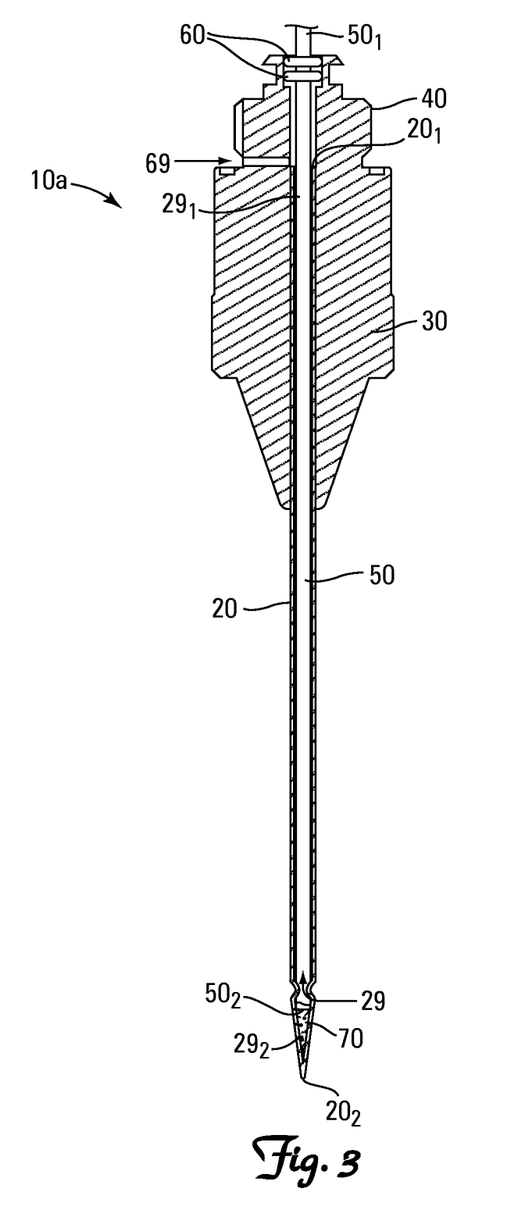
FIG. 3 is an enlarged cross-sectional side view of the needle and collar components of the invention depicted in FIG. 1.
Figure 4:
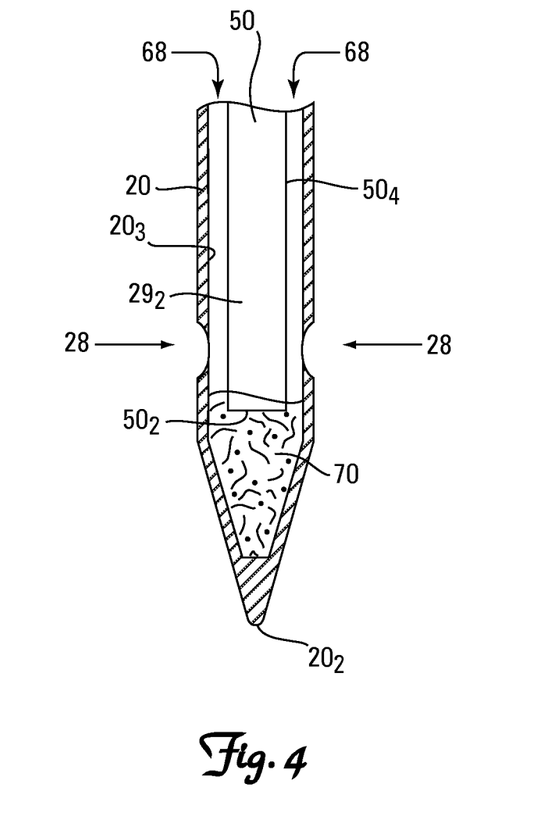
FIG. 4 is an enlarged cross-sectional side view of the distal end portion of the needle component of the invention depicted in FIG. 1.

Referring generally to FIGS. 2, 3 and 4 the needle 20 has a longitudinal lumen 29 with at least one port 28 proximate the distal tip $20_2$ of the needle 20. The port 28 is preferably a lateral side port 28 with the needle 20 preferably having at least two diametrically opposed lateral side ports 28. The needle 20 can be a sharp tipped or blunt tipped needle 20 and preferably has a nominal inner diameter (i.e., lumen 29) of between 1.0 to 3.5 mm.

The proximal end $20_1$ of the needle 20 is preferably attached to a collar 30 via brazing, soldering or gluing, suitable for threadable attachment to the optical block subassembly 10b of the instrument 10 via a thread fitting 40.

The at least one fiber optic filament 50 extends axially along the length of the lumen 29 from a proximal end $50_1$ proximate the proximal end $29_1$ of the lumen 29 to a distal end $50_2$ proximate the distal end $29_2$ of the lumen 29 and in sensing communication with the photoluminescent analyte-partial-pressure-sensitive probe 70. The outside diameter of the at least one fiber optic filament 50 is smaller than the inside diameter of the needle 20 so as to form a void volume channel 68 along the length of the lumen 29. As a result of the inherent axial curvature and flexibility of typical fiber optic filaments 50, the void volume channel 68 may be an amorphous channel. The proximal end $50_1$ of the fiber optic filament 50 is preferably sealingly engaged to the inner surface $20_3$ of the needle 20 or the inner surface (not separately numbered) of the bore (not separately numbered) of the collar 30 by a suitable sealing means such as a sealant (e.g., epoxy) or one or more o-rings 60, to secure the at least one fiber optic filament 50 within the lumen 29 and prevent the atmosphere located outside a structure S being tested from reaching and contaminating the photoluminescent analyte-sensitive probe 70 and/or the pressure sensor 90 through the annular interface between the inner surface $20_3$ of the needle 20 and the outer surface $50_4$ of the fiber optic filament 50.

The photoluminescent analyte-sensitive probe 70 is located within the lumen 29 between the distal tip $50_2$ of the at least one fiber optic filament 50 and the distal tip $20_2$ of the needle 20, and is in sensing fluid communication with the external environment, such as a volume V enclosed by a structure S, through the at least one port 28 in the needle 20.

The photoluminescent analyte-partial-pressure-sensitive probe 70 can be selected from the numerous commercially available types of such probes. Generally, such probes comprise a carrier substrate coated with an analyte-sensitive photoluminescent dye, often with the analyte-sensitive photoluminescent dye embedded within an analyte-permeable polymer matrix.

When employed, the carrier substrate may be selected from any material possessing sufficient structural integrity to physically support the analyte-sensitive photoluminescent dye and capable of withstanding extended exposure to the environment into which the probe 70 is to be used (e.g., high humidity, low humidity, submerged in water, submerged in an acidic solution, etc). Materials suitable for use as the carrier substrate, dependent of course upon the environment to which the probe 70 is to be exposed during normal usage, include specifically but not exclusively, cellulosics such as paper, wax paper, cardstock, cardboard, wood and wood laminates; plastics such as polyethylene, polypropylene and polyethylene terephthalate; metals such as aluminum sheets, aluminum foil, steel and tin; woven and unwoven fabrics; glass; and various combinations and composites thereof such a mylar.

The analyte-sensitive photoluminescent dye may be selected from any of the well-known analyte-sensitive photoluminescent dyes. One of routine skill in the art is capable of selecting a suitable dye based upon the intended use of the fiber optic analyte-sensing instrument 10. For example, a nonexhaustive list of suitable oxygen-sensitive photoluminescent dyes includes specifically, but not exclusively, ruthenium(II)-bipyridyl and ruthenium(II)-diphenylphenanothroline complexes, porphyrin-ketones such as platinum(II)-octaethylporphine-ketone, platinum(II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium(III) or osmium(II).

Typically, the analyte-sensitive photoluminescent dye is compounded with a suitable analyte-permeable polymer matrix. Again, one of routine skill in the art is capable of selecting a suitable analyte-permeable polymer matrix based upon the intended use of the fiber optic analyte-sensing instrument 10. For example, a nonexhaustive list of suitable polymers for use as an oxygen-permeable polymer matrix includes specifically, but not exclusively, polystryrene, polycarbonate, polysulfone, polyvinyl chloride and some co-polymers.

Referring to FIG. 3, the proximal end $50_1$ of the at least one fiber optic filament 50 is in optical communication with a photoluminescence detector 80 for transmitting excitation radiant energy from a source of excitation radiant energy 81 to the photoluminescent analyte-partial-pressure-sensitive probe 70, and thereafter transmitting radiant energy emitted by the excited probe 70 back to the photoluminescence detector 80 where a $P_{ANALYTE}$ electrical signal, representative of the analyte-partial-pressure of a fluid in fluid communication with the probe 70 is generated. The radiant energy emitted by the excited probe 70 can be measured in terms of intensity and/or lifetime (rate of decay, phase shift or anisotropy), with measurement of lifetime generally preferred as a more accurate and reliable measurement technique when seeking to establish analyte concentration via measurement of the extent to which an analyte-sensitive photoluminescent dye has been quenched by the analyte.

Referring to FIG. 3, the void volume channel 68 is in pressure communication with a pressure sensor 90 for communicating sample-fluid total pressure (i.e., the total pressure of the fluid in sensing fluid communication with the photoluminescent analyte-partial-pressure-sensitive probe 70) to the pressure sensor 90, whereby the pressure sensor 90 can generate a $P_{TOTAL}$ electronic signal representative of the sample-fluid total-pressure in fluid communication with the probe 70. A diaphragm (not shown) may be interposed between the pressure sensor 90 and a sample-fluid in communication with the probe 70, but is generally unnecessary. Hence, the pressure sensor 90 may typically be in direct fluid communication with the sample-fluid communicating with the probe 70. Referring to FIG. 3, in order to facilitate placement of the pressure sensor 90 at a convenient location in the handle of the instrument 10, a branch channel 69 may be provided to fluidly connect a remotely located pressure sensor 90 with the void volume channel 68.

A user actuated trigger 120 is provided for initiating the taking of temporally paired readings of $P_{TOTAL}$ and $P_{ANALYTE}$ by the pressure sensor 90 and the photoluminescence detector 80, respectively. The $P_{TOTAL}$ and $P_{ANALYTE}$ readings may be taken in serial or parallel fashion, but are preferably taken simultaneously.

Temporally paired readings of $P_{TOTAL}$ and $P_{ANALYTE}$ are transmitted from the pressure sensor 90 and the photoluminescence detector 80, respectively, to a microprocessor 100 programmed to calculate an analyte concentration (ANALYTE %) from these temporally paired electrical signals based at least in part upon the algorithm ANALYTE %=$P_{ANALYTE}/P_{TOTAL}$, and display the calculated analyte concentration on an electronic display 110. The microprocessor 100 and display 110 may be located remotely from the instrument 10 and wired or wirelessly communicate with the pressure sensor 90 and the photoluminescence detector 80, but are preferably integrated into the handle of the instrument 10.

Manufacture

The fiber optic analyte-sensing needle 10 can be assembled by (a) affixing the needle 20 to the collar 30, such as by brazing, (b) inserting the probe 70 into the lumen 29 of the needle 20 from the open proximal end $29_1$ of the lumen 29 and tamping the probe 70 into the lumen 29 until it is positioned proximate the distal tip $20_2$ of the needle 20, (c) threading the at least one fiber optic filament 50 into the lumen 29 of the needle 20 from the open proximal end $29_1$ of the lumen 29 until the distal tip $50_2$ of the at least one fiber optic filament 50 is positioned proximate the probe 70 at the distal tip $20_2$ of the needle 20, (d) sliding the void volume channel sealing o-ring (s) 60 onto the proximal end $50_1$ of the at least one fiber optic filament 50 projecting from the bore (not separately numbered) of the collar 30 and into seated arrangement into the annular interface between the inner surface (not separately numbered) of the collar 30 and the outer surface $50_4$ of the fiber optic filament 50 to form a collared needle subassembly 10a, (e) sealing securing the proximal end of the collared needle subassembly 10a to an optical block housing the photoluminescence detector 80 and source of excitation radiant energy 81 employing a thread fitting 40 and inner and outer o-rings 41 and 42 respectively, to form an optical block subassembly 10b, and (f) attaching the optical block subassembly 10b to the balance of the electronics housed within a handle subassembly 10c with the pressure sensor 90 in the handle subassembly 10c in sealed pressure communication with the void volume channel 68 in the optical block subassembly 10b and the microprocessor 100 in the handle subassembly 10c in electrical communication with the photoluminescence detector 80 in the optical block subassembly 10b.

Use

The fiber optic analyte-sensing instrument 10 can be used to quickly, easily, accurately and reliably measure analyte concentration within a defined space, typically an enclosed volume V, even though the enclosed volume V may have a total pressure ($P_{TOTAL}$) which differs substantially from surrounding atmospheric pressure. Briefly, the fiber optic analyte-sensing instrument 10 can be used to measure analyte concentration within a defined volume V by (A) placing the distal end portion $20_2$ of the needle 20 into fluid communication with a defined space to be tested, such as by placing the distal end portion $20_2$ of the needle 20 into fluid communication with the volume V of a hermetically sealed package S so as to place the distal end $29_2$ of the lumen 29 into fluid communication with the volume V enclosed by the package S, whereby both the analyte-partial-pressure-sensitive photoluminescent probe 70 and the pressure sensor 90 on the instrument 10 are placed into sensible communication with the enclosed volume V, (B) allowing the concentration of analyte in sensible communication with the photoluminescent probe 70 to equilibrate with the analyte concentration within the enclosed volume V, (C) allowing the pressure in sensible communication with the pressure sensor 90 to equilibrate with the pressure of the enclosed volume V, and (D) ascertaining an analyte concentration within the enclosed volume V by: (i) measuring the total pressure of the enclosed volume V with the equilibriated pressure sensor 90, (ii) exposing the equilibriated photoluminescent probe 70 to excitation radiation, (iii) measuring radiation emitted by the excited photoluminescent probe 70, and (iv) converting the measured emission to an analyte concentration based upon a known pressure compensated conversion algorithm that employs the value of the measured total pressure ($P_{TOTAL}$) of the enclosed volume V to pressure correct the converted measured emission.

The fiber optic analyte-sensing instrument 10 can also be used to quickly, easily, accurately and reliably monitoring changes in analyte concentration within a defined space, typically an enclosed volume V, even though the enclosed volume V may have a total pressure ($P_{TOTAL}$) which differs substantially from surrounding atmospheric pressure. Briefly, the fiber optic analyte-sensing instrument 10 can be used to monitoring changes in analyte concentration within a defined volume V by (A) placing the distal end portion $20_2$ of the needle 20 into fluid communication with a defined space to be tested, such as by placing the distal end portion $20_2$ of the needle 20 into fluid communication with the volume V of a hermetically sealed package S so as to place the distal end $29_2$ of the lumen 29 into fluid communication with the volume V enclosed by the package S, whereby both the analyte-partial-pressure-sensitive photoluminescent probe 70 and the pressure sensor 90 on the instrument 10 are placed into sensible communication with the enclosed volume V, (B) allowing the concentration of analyte in sensible communication with the photoluminescent probe 70 to equilibrate with the analyte concentration within the enclosed volume V, (C) allowing the pressure in sensible communication with the pressure sensor 90 to equilibrate with the pressure of the enclosed volume V, and (D) ascertaining an analyte concentration within the enclosed volume V by: ($\alpha$) coincidentally and repeatedly measuring the total pressure ($P_{TOTAL}$) of the enclosed volume V with the equilibriated pressure sensor 90, and the partial pressure of analyte ($P_{ANALYTE}$) in the enclosed volume V with the equilibriated photoluminescent probe 70, ($\beta$) measuring passage of time ($\Delta t$) during the repeated coincidental measurements, and ($\gamma$) converting at least some of the coincidental measurements to an analyte concentration (ANALYTE %) based upon a known pressure compensated conversion algorithm that employs the value of the measured total pressure ($P_{TOTAL}$) of the enclosed volume V, and (E) reporting at least one of ($\alpha$) at least two ascertained analyte concentrations (ANALYTE %) and the time interval ($\Delta t$) between those reported concentrations, and ($\beta$) a rate of change in analyte concentration within the enclosed volume V calculated from data obtained in step (D).

We claim:

1. An in situ analyte-sensing fiber optic instrument, comprising (i) a tube having a distal end and an inner surface defining a lumen, (ii) an analyte-partial-pressure-sensitive photoluminescent probe located proximate a distal end of the lumen and in fluid communication with a fluid occupying a volume external to the distal end of the tube through an opening in the tube, and (iii) at least one fiber optic filament having an outer surface, extending axially along the length of the lumen and in optical communication with the analyte-partial-pressure-sensitive photoluminescent probe, the instrument further comprising:

(a) a void volume channel extending axially along the length of the lumen between the inner surface of the tube and the outer surface of the at least one fiber optic filament, and (b) a pressure sensor in pressure communication via the void volume channel in the lumen of the tube with the fluid from the volume communicating with the analyte-partial-pressure-sensitive photoluminescent probe via the opening in the tube.

2. The in situ analyte-sensing fiber optic instrument of claim 1 wherein the pressure sensor generates a $P_{TOTAL}$ electronic signal representative of the total-pressure of a fluid in fluid communication with the probe, and the instrument further comprises:

(a) a detector in optical communication with the analyte-partial-pressure-sensitive photoluminescent probe via the at least one fiber optic filament for receiving radiant energy emitted by the probe and generating a $P_{ANALYTE}$ electrical signal representative of the analyte-partial-pressure of a fluid in fluid communication with the probe, (b) a microprocessor in electrical communication with the pressure sensor and the detector for receiving temporally paired $P_{TOTAL}$ and $P_{ANALYTE}$ electrical signals respectively, and calculating an analyte concentration from the temporally paired electrical signals based upon an algorithm ANALYTE $\% = P_{ANALYTE}/P_{TOTAL}$, and (c) an electronic display in electrical communication with the microprocessor for displaying calculated analyte concentration values.

3. The in situ analyte-sensing fiber optic instrument of claim 2 further comprising a user activatable trigger operable for simultaneously generating temporally paired $P_{TOTAL}$ and $P_{ANALYTE}$ electrical signals each time the trigger is activated.

4. The in situ analyte-sensing fiber optic instrument of claim 1 wherein the tube is a blunt-tipped needle with a nominal inner diameter of 1.0 to 3.5 mm.

5. The in situ analyte-sensing fiber optic instrument of claim 1 wherein the tube is a sharp-tipped needle with a nominal inner diameter of 1.0 to 3.5 mm.

6. The in situ analyte-sensing fiber optic instrument of claim 1 wherein the void volume channel is an amorphous channel.

7. The in situ analyte-sensing fiber optic instrument of claim 1 wherein the pressure sensor is in fluid communication with fluid communicating with the analyte-partial-pressure-sensitive photoluminescent probe via the void volume channel in the lumen of the tube.

8. A method for measuring an analyte concentration within a space enclosed by a structure, comprising the steps of:

(a) obtaining an analyte-sensing fiber optic instrument according to claim 1, (b) penetrating the structure with the tube of the instrument so as to place the distal end of the lumen into fluid communication with the space enclosed by the structure, whereby both the analyte-partial-pressure-sensitive photoluminescent probe and the pressure sensor on the instrument are placed into sensible communication with the enclosed space, (c) allowing the concentration of analyte in sensible communication with the photoluminescent probe to equilibrate with the analyte concentration within the enclosed space, (d) allowing the pressure in sensible communication with the pressure sensor to equilibrate with the pressure of the enclosed space, and (e) ascertaining an analyte concentration within the enclosed space by: (i) measuring the total pressure of the enclosed space with the equilibriated pressure sensor to obtain a measured total pressure value for the enclosed space, (ii) exposing the equilibriated photoluminescent probe to excitation radiation, (iii) measuring radiation emitted by the excited photoluminescent probe, and (iv) converting the measured emission to an analyte concentration based upon a known pressure compensated conversion algorithm that employs the measured total pressure value for the enclosed space.

9. The method of claim 8 wherein the analyte is oxygen.

10. The method of claim 9 wherein the space is a retention chamber of a hermetically sealed package containing an oxygen labile pharmaceutical or foodstuff.

11. A handheld instrument for impromptu in situ concomitant sensing of oxygen partial pressure and total pressure of a hermetically sealed volume, comprising an integrated combination of at least:

(a) a hollow shank having a proximal end, a distal end and an inner surface defining a lumen in fluid communication with a volume external to the distal end, (b) an oxygen-partial-pressure-sensitive photoluminescent probe within the lumen proximate the distal end of the shank and in fluid communication with a fluid occupying a volume external to the distal end of the shank through an opening in the shank, (c) an electronics package proximate the proximal end of the shank, including at least:
  (i) a source of excitation radiant energy,
  (ii) a photoluminescence detector, and
  (iii) a pressure sensor, and (d) at least one fiber optic filament having an outer surface and extending axially along the length of the lumen operable for (i) transmitting excitation radiant energy from the source of excitation radiant energy to the oxygen-partial-pressure-sensitive photoluminescent probe, and (ii) transmitting radiant energy emitted by the oxygen-partial-pressure-sensitive photoluminescent probe to the photoluminescence detector, and configured relative to the lumen to form a void volume channel extending axially along the length of the lumen between the inner surface of the shank and the outer surface of the at least one fiber optic filament, wherein (e) the pressure sensor is in pressure communication via the void volume channel in the lumen of the shank with the fluid from the volume communicating with the oxygen-partial-pressure-sensitive photoluminescent probe via the opening in the shank.

12. The handheld instrument of claim 11 wherein (i) the photoluminescence detector generates a $P_{OXYGEN}$ electrical signal representative of the oxygen-partial-pressure of a fluid in fluid communication with the probe, (ii) the pressure sensor generates a $P_{TOTAL}$ electronic signal representative of the total-pressure of a fluid in fluid communication with the probe, and the electronics package further comprises:

(a) a microprocessor in electrical communication with the photoluminescence detector and the pressure sensor for receiving temporally paired $P_{OXYGEN}$ and $P_{TOTAL}$ electrical signals respectively, and calculating an oxygen concentration from the temporally paired electrical signals based upon the algorithm OXYGEN $\% = P_{OXYGEN}/P_{TOTAL}$, and (b) an electronic display in electrical communication with the microprocessor for displaying calculated oxygen concentration values.

13. The handheld instrument of claim 12 further comprising a user activatable trigger operable for simultaneously generating temporally paired $P_{TOTAL}$ and $P_{OXYGEN}$ electrical signals each time the trigger is activated.

14. A method for monitoring changes in oxygen concentration within a space enclosed by a structure, comprising the steps of:
(a) obtaining an instrument according to claim 12,
(b) penetrating the structure with the hollow shank of the instrument so as to place a distal end of the lumen into fluid communication with the space enclosed by the structure, whereby both the oxygen-partial-pressure-sensitive photoluminescent probe and the pressure sensor on the instrument are placed into sensible communication with the enclosed space,
(c) allowing the concentration of oxygen in sensible communication with the photoluminescent probe to equilibrate with the oxygen concentration within the enclosed space,
(d) allowing the pressure in sensible communication with the pressure sensor to equilibrate with the pressure of the enclosed space,
(e) ascertaining an oxygen concentration within the enclosed space over time by: (i) coincidentally and repeatedly measuring the total pressure of the enclosed space with the equilibriated pressure sensor to obtain a measured total pressure value for the enclosed space, and the partial pressure of oxygen in the enclosed spaced with the equilibriated photoluminescent probe, (ii) measuring passage of time during the repeated coincidental measurements to establish a time interval between repeated coincidental measurements, and (iii) converting at least some of the coincidental measurements to an oxygen concentration based upon a known pressure compensated conversion algorithm that employs the measured total pressure value for the enclosed space, and
(f) reporting at least one of (i) at least two ascertained oxygen concentrations and the time interval between those reported concentrations, and (ii) a rate of change in oxygen concentration within the enclosed space calculated from data obtained in step (e).

15. The method of claim 14 wherein the space is a retention chamber of a hermetically sealed package containing an oxygen labile pharmaceutical or foodstuff.

16. The handheld instrument of claim 11 wherein the shank is a blunt-tipped needle with a nominal inner diameter of 1.0 to 3.5 mm.

17. The handheld instrument of claim 11 wherein the shank is a sharp-tipped needle with a nominal inner diameter of 1.0 to 3.5 mm.

18. The handheld instrument of claim 11 wherein the void volume channel is an amorphous channel.

19. The handheld instrument of claim 11 wherein the pressure sensor is in fluid communication with fluid communicating with the oxygen-partial-pressure-sensitive photoluminescent probe via the void volume channel in the lumen of the shank.

* * * * *